United States Patent
Nessel

(10) Patent No.: US 10,436,619 B2
(45) Date of Patent: Oct. 8, 2019

(54) FLOW RATE SENSOR

(71) Applicant: SANOFI-AVENTIS DEUTSCHLAND GMBH, Frankfurt am Main (DE)

(72) Inventor: Christian Nessel, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 143 days.

(21) Appl. No.: 15/543,452

(22) PCT Filed: Jan. 14, 2016

(86) PCT No.: PCT/EP2016/050666
§ 371 (c)(1),
(2) Date: Jul. 13, 2017

(87) PCT Pub. No.: WO2016/113349
PCT Pub. Date: Jul. 21, 2016

(65) Prior Publication Data
US 2018/0149502 A1 May 31, 2018

(30) Foreign Application Priority Data
Jan. 16, 2015 (EP) .................................. 15151371

(51) Int. Cl.
*G01F 1/56* (2006.01)
*G01F 1/58* (2006.01)
(Continued)

(52) U.S. Cl.
CPC ............. *G01F 1/582* (2013.01); *A61M 5/142* (2013.01); *A61M 5/16831* (2013.01);
(Continued)

(58) Field of Classification Search
CPC .. G01F 1/582; G01F 1/60; G01F 1/56; A61M 5/16886; A61M 5/16831; A61M 5/142; A61M 2205/3317; A61M 2005/16863
See application file for complete search history.

(56) References Cited

U.S. PATENT DOCUMENTS

| 2005/0034534 | A1  | 2/2005 | Harnett et al. |
| 2007/0220992 | A1* | 9/2007 | Lam .......................... G01F 1/58 |
|              |     |        | 73/861.15 |

(Continued)

FOREIGN PATENT DOCUMENTS

| EP | 0228883 | 7/1987 |
| EP | 1762263 | 3/2007 |
| WO | WO 2013/062474 | 5/2013 |

OTHER PUBLICATIONS

International Preliminary Report on Patentability in International Application No. PCT/EP2016/050666, dated Jul. 18, 2017, 8 pages.
(Continued)

*Primary Examiner* — Xin Y Zhong
(74) *Attorney, Agent, or Firm* — Fish & Richardson P.C.

(57) ABSTRACT

The disclosure relates to a flow rate sensor for determining a flow rate of a liquid within a tube, the flow rate sensor comprising at least one coil arranged in the vicinity of the tube in such a manner that an eddy current in the liquid due to the liquid's flowing affects an impedance of the coil.

18 Claims, 5 Drawing Sheets

(51) Int. Cl.
*A61M 5/142* (2006.01)
*A61M 5/168* (2006.01)
*G01F 1/60* (2006.01)

(52) U.S. Cl.
CPC ........... *A61M 5/16886* (2013.01); *G01F 1/56* (2013.01); *G01F 1/60* (2013.01); *A61M 2005/16863* (2013.01); *A61M 2205/3317* (2013.01)

(56) References Cited

U.S. PATENT DOCUMENTS

| | | |
|---|---|---|
| 2007/0234821 A1 | 10/2007 | Wehrs et al. |
| 2008/0016967 A1 | 1/2008 | Schrag et al. |
| 2008/0262796 A1* | 10/2008 | Rufer ............... G01F 1/584 702/184 |
| 2010/0024569 A1* | 2/2010 | Ehrenberg ......... G01F 1/586 73/861.12 |
| 2013/0141117 A1 | 6/2013 | Nikolenko |
| 2014/0297203 A1* | 10/2014 | Liao ................. A01J 5/01 702/47 |

OTHER PUBLICATIONS

International Search Report and Written Opinion in International Application No. PCT/EP2016/050666, dated Jun. 20, 2016, 11 pages.

* cited by examiner

FLOW RATE SENSOR

CROSS-REFERENCE TO RELATED APPLICATIONS

This application is a U.S. national stage application under 35 USC § 371 of International Application No. PCT/EP2016/050666, filed on Jan. 14, 2016, which claims priority to European Patent Application No. 15151371.0, filed on Jan. 16, 2015, the entire contents of which are incorporated herein by reference.

TECHNICAL FIELD

The disclosure relates to a flow rate sensor.

BACKGROUND

In drug delivery devices such as insulin pumps, occlusion detection is desirable as a safety feature. Occlusions may typically be detected by measuring parameters in a pump chamber or by a flow sensor.

SUMMARY

Certain aspects of the present disclosure can be implemented to provide an improved flow sensor.

Certain aspects of the present disclosure can be implemented as a flow sensor according to claim 1.

Exemplary embodiments of the disclosure are given in the dependent claims.

According to the disclosure, a flow rate sensor for determining a flow rate of a liquid within a tube comprises at least one coil arranged in the vicinity of the tube in such a manner that an eddy current in the liquid due to the liquid's flowing affects an impedance of the coil. The impedance of a coil is a complex quantity, the real part of which is related to the flow rate. An occlusion or other type of contamination within the tube near the coils will substantially alter the flow rate and hence the eddy current in the liquid thereby also altering the impedance of the respective coil. This allows for contactless determination of a flow rate or disturbances of the flow of the liquid as may occur due to contaminations, occlusions or air bubbles.

A change of drug or contamination will change the relation between the real part and the imaginary part of the impedance. Thus, the type or the contamination of the drug can be determined by the impedance.

In an exemplary embodiment, the flow rate sensor comprises a first coil and a second coil, the first coil arranged in the vicinity of a first section of the tube, the first section having a first diameter, the second coil arranged in the vicinity of a second section of the tube, the second section having a second diameter, which may be different from the first diameter. The relation of the impedances of the first coil and the second coil to the known first diameter and second diameter allow for detecting contaminations.

In an exemplary embodiment, the at least one coil is arranged about the tube.

In an exemplary embodiment, the at least one coil is connected to a measuring unit adapted to determine the impedance of the at least one coil.

In an exemplary embodiment, the at least one coil is arranged about a respective magnetic guide having one or two air gaps in which the tube is received. Due to the magnetic guide, the coupling of the magnetic flux to the liquid in the tube is improved so that the eddy current is higher and consequently the impedance change is higher.

In an exemplary embodiment, the at least one coil is arranged next to the tube at a predetermined distance, wherein at least in the vicinity of the coil the tube is flexible to such an extent that the tube can expand depending on a pressure of the liquid. The liquid, e.g. a medicament, flowing through the tube causes a stretching of the tube thus changing the eddy current and altering the impedance of the coil. In case two coils are arranged next to two flexible tube sections with different diameters, the relation of the first diameter to the second diameter is known such that the flow rate can be determined by the expansion of the tube sections.

In an exemplary embodiment, a thickness of a wall of the tube is taken into account in the predetermined distance such that the distance is actually the distance of the coil to a surface of the liquid contacting the wall of the tube from inside.

In an exemplary embodiment, the magnetic guide is arranged as a cup-core ferrite arranged about the tube, wherein the respective coil is arranged within the magnetic guide. A magnetic flux of a magnetic field generated by the coil is at least nearly entirely guided by the magnetic guide such that at least a part, in particular at least nearly all magnetic flux lines cross the tube.

In an exemplary embodiment, the magnetic guide comprises an arcuate base member with a semicircular or crescent cross section and a plurality of, inwardly directed protrusions having tips, between which respective air gaps are provided, wherein at least one coil is arranged on at least one of the protrusions, wherein a tube is arranged in the air gaps between the inward tips of the protrusions such that the tube is contacted by the tips of the protrusions at angular offsets. The air gaps are thus big enough ensuring that almost all magnetic flux lines cross the tube on a small area.

In an exemplary embodiment, the protrusions are arranged as spikes originating from the base member.

In an exemplary embodiment, the tips of the protrusions are angularly offset by substantially 90°. Other offset angles are also possible.

In an exemplary embodiment, the at least one coil consists of a number of cascaded coils, electrically connected in series.

The flow rate sensor may be part of a drug delivery device, further comprising at least one tube for a liquid whose flow rate is to be determined.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given hereinbelow and the accompanying drawings which are given by way of illustration only, and thus, are not limitive of the present disclosure, and wherein.

Corresponding parts are marked with the same reference symbols in all figures.

DETAILED DESCRIPTION

Figure 1:
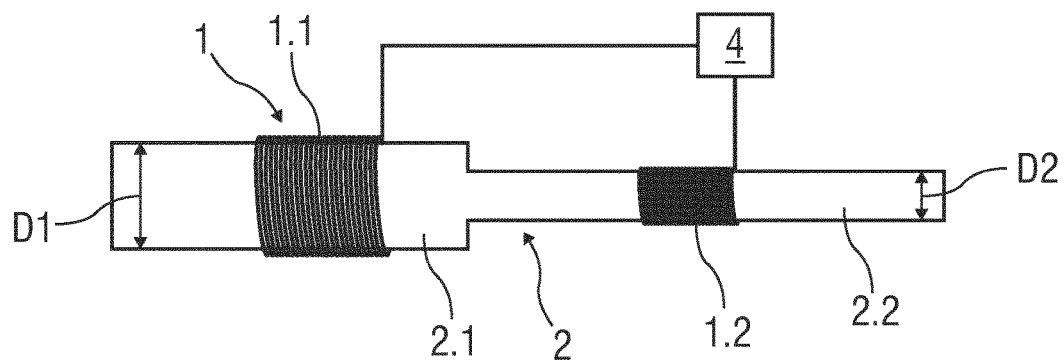
FIG. 1 is a schematic view of an exemplary first embodiment of a flow rate sensor.

FIG. 1 is a schematic view of an exemplary first embodiment of a flow rate sensor 1. The flow rate sensor 1 may be used for contactless detection of occlusions or contaminations, e. g. air bubbles in a liquid within a tube 2 of a drug delivery device, e. g. an insulin pump. Likewise, the flow rate sensor 1 may be used for detecting the type of drug within the tube 2.

One end of the tube 2 may be connected to a drug delivery device and the other end may be connected to a hypodermic needle (not illustrated). The tube 2 comprises a first section 2.1 having a first diameter D1 and a second section 2.2 having a second diameter D2 different from the first diameter. The flow rate sensor 1 comprises a first coil 1.1 arranged about the first section 2.1 and a second coil 1.2 arranged about the second section 2.2. The first coil 1.1 and the second coil 1.2 are connected to a measuring unit 4 in order to determine impedances of the first coil 1.1 and the second coil 1.2. A liquid, e. g. a medicament, flowing through the tube 2 causes an eddy current thereby altering the impedance of the coils 1.1, 1.2.

The impedance of a coil is a complex quantity, the real part of which is related to the flow rate. A relation of the imaginary part to the real part is specific for each material thus allowing for detecting the type of drug within the tube 2.

The relation of the impedances of the first coil 1.1 and the second coil 1.2 to the known first diameter D1 and second diameter D2 allow for detecting contaminations. The flow rate may be determined by dividing the impedance of the first section by the impedance of the second section multiplied by a design related factor.

An occlusion within the tube 2 near one of the coils 1.1, 1.2 will substantially alter the flow rate and hence the eddy current in the liquid thereby also altering the impedance of the respective coil 1.1, 1.2. The contamination may hence be detected by the changing relation of the complex impedance.

Figure 2:
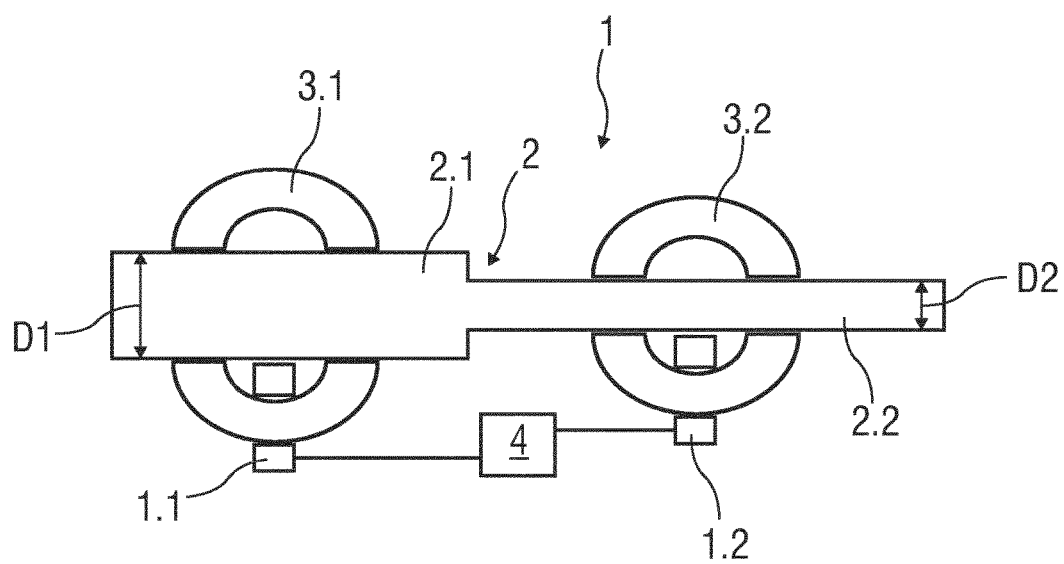
FIG. 2 is a schematic view of an exemplary second embodiment of a flow rate sensor.

FIG. 2 is a schematic view of an exemplary second embodiment of a flow rate sensor 1.

The flow rate sensor 1 may be used for contactless detection of occlusions or contaminations, e. g. air bubbles in a tube 2 of a drug delivery device, e. g. an insulin pump.

One end of the tube 2 may be connected to a drug delivery device and the other end may be connected to a hypodermic needle (not illustrated). The tube 2 comprises a first section 2.1 having a first diameter D1 and a second section 2.2 having a second diameter D2 different from the first diameter. The flow rate sensor 1 comprises a first coil 1.1 and a second coil 1.2. The first coil 1.1 is arranged about a first magnetic guide 3.1 having one or two air gaps in which the first section 2.1 is received. The second coil 1.2 is arranged about a second magnetic guide 3.2 having one or two air gaps in which the second section 2.2 is received. The first coil 1.1 and the second coil 1.2 are connected to a measuring unit 4 in order to determine impedances of the first coil 1.1 and the second coil 1.2. A liquid, e. g. a medicament, flowing through the tube 2 causes an eddy current thereby altering the impedance of the coils 1.1, 1.2. Due to the first and second magnetic guides 3.1, 3.2 the coupling of the magnetic flux to the liquid in the tube 2 is improved so that the eddy current is higher than in the first embodiment and consequently the impedance change is higher.

Figure 3:
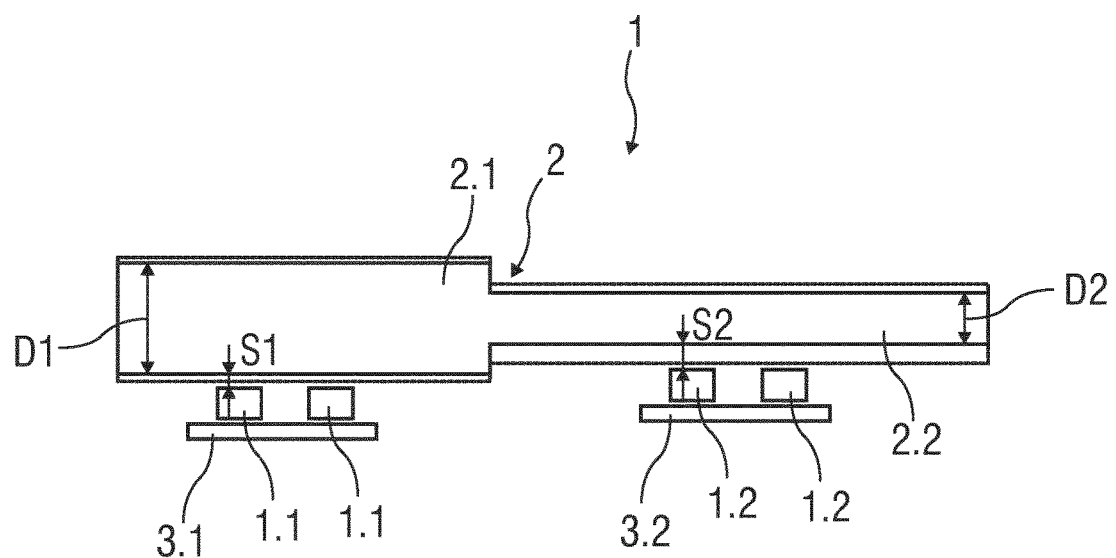
FIG. 3 is a schematic view of an exemplary third embodiment of a flow rate sensor.

FIG. 3 is a schematic view of an exemplary third embodiment of a flow rate sensor 1. The flow rate sensor 1 may be used for contactless detection of occlusions or contaminations, e. g. air bubbles in a tube 2 of a drug delivery device, e. g. an insulin pump.

One end of the tube 2 may be connected to a drug delivery device and the other end may be connected to a hypodermic needle (not illustrated). The tube 2 comprises a first section 2.1 having a first diameter D1 and a second section 2.2 having a second diameter D2 different from the first diameter. The flow rate sensor 1 comprises a first coil 1.1 arranged next to the first section 2.1 at a first distance S1 and a second coil 1.2 arranged next to the second section 2.2 at a second distance S2. The first coil 1.1 and the second coil 1.2 are connected to a measuring unit 4 in order to determine impedances of the first coil 1.1 and the second coil 1.2. At least in the first section 2.1 and in the second section 2.2 the tube 2 is flexible to such an extent that the tube 2 can expand depending on a pressure of the liquid thereby varying the first diameter D1 and/or the second diameter D2 and consequently the first and second distance S1, S2. A liquid, e. g. a medicament, flowing through the tube 2 causes a stretching of the tube 2 thus changing the eddy current and altering the impedance of the coils 1.1, 1.2. As the relation of the first diameter D1 to the second diameter D2 is known, the flow rate can be determined. The flow rate is determined by dividing the impedance of the first section by the impedance of the second section multiplied by a design related factor.

In an exemplary embodiment a thickness of a wall of the tube 2 is taken into account such that the first and second distance S1, S2 is actually the respective distance of the first and second coil 1.1, 1.2 to a surface of the liquid contacting the wall of the tube 2.

Figure 4:
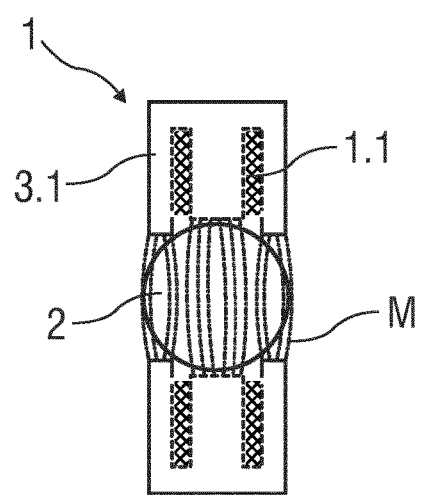
FIG. 4 is a schematic view of an exemplary fourth embodiment of a flow rate sensor with a cup-core ferrite and a coil arranged about a tube.
Figure 5:
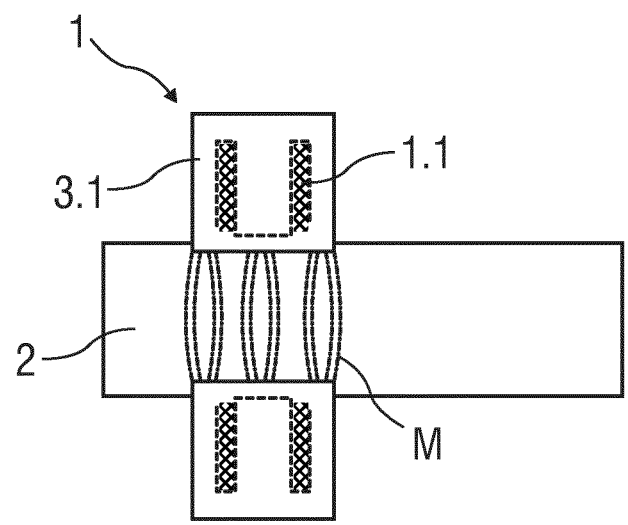
FIG. 5 is another schematic view of the fourth embodiment.
Figure 6:
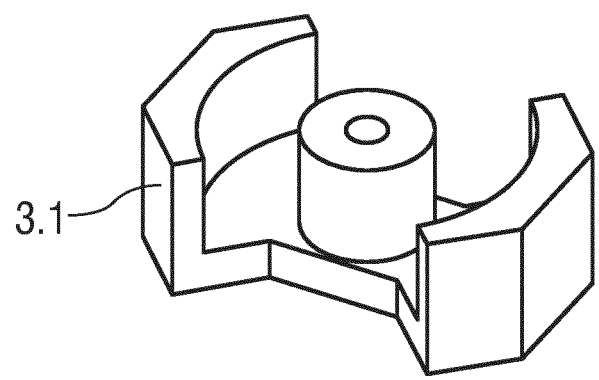
FIG. 6 is a schematic perspective view of the cup-core ferrite

FIG. 4 is a schematic view of an exemplary fourth embodiment of a flow rate sensor 1 with a magnetic guide 3.1 in the form of a cup-core ferrite arranged about a tube 2, wherein a coil 1.1 is arranged within the magnetic guide 3.1. FIG. 5 is another schematic view of the fourth embodiment. A magnetic flux of a magnetic field generated by the coil 1.1 and represented by magnetic flux lines M is at least nearly entirely guided by the magnetic guide 3.1 such that at least a part, in particular at least nearly all magnetic flux lines M cross the tube 2. FIG. 6 is a schematic perspective view of the magnetic guide 3.1 of the fourth embodiment, wherein the coil 3.1 is not shown for clarity. The same set-up may be used for the first coil 1.1 with the first magnetic guide 3.1 and the second coil 1.2 with the second magnetic guide 3.2.

Figure 7:
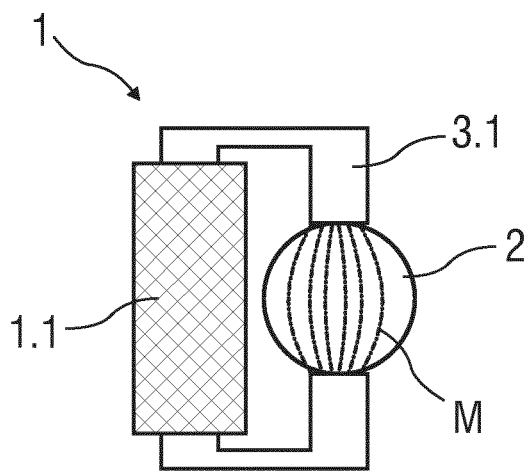
FIG. 7 is a schematic view of an exemplary fifth embodiment of a flow rate sensor with a ferrite forming a magnetic circuit with an air gap, a coil and a tube arranged in the air gap.
Figure 8:
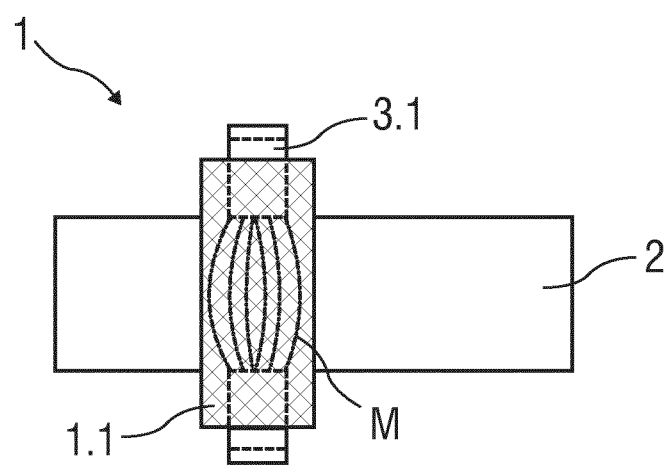
FIG. 8 is another schematic view of the fifth embodiment.

FIG. 7 is a schematic view of an exemplary fifth embodiment of a flow rate sensor 1 with a magnetic guide 3.1, e. g. a ferrite forming a magnetic circuit with an air gap, wherein a coil 1.1 is arranged about the magnetic guide 3.1 and a tube 2 is arranged in the air gap. FIG. 8 is another schematic view of the fifth embodiment. In this embodiment an outside of the coil 1.1 is not covered by a ferrite material such that a proportion of the magnetic flux lines M is guided by the magnetic guide 3.1 such that at least a part of the magnetic flux lines M cross the tube 2.

Figure 9:
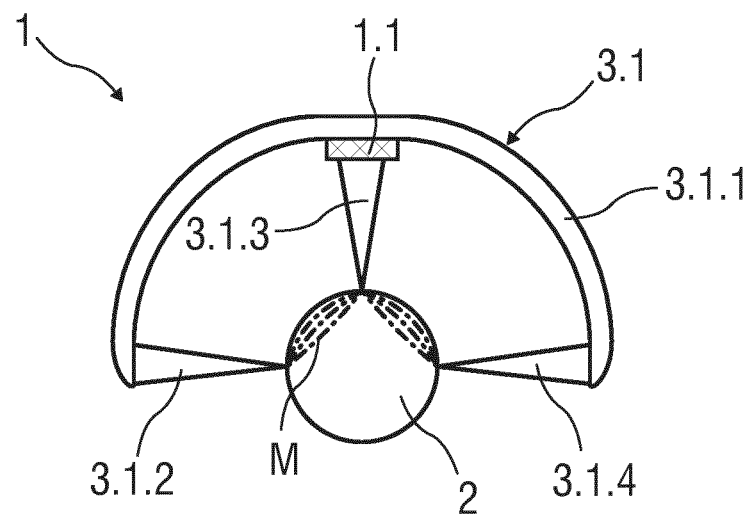
FIG. 9 is a schematic view of an exemplary sixth embodiment of a flow rate sensor with an arcuate ferrite having inward protrusions forming a magnetic circuit with air gaps, a coil and a tube arranged in the air gaps.
Figure 10:
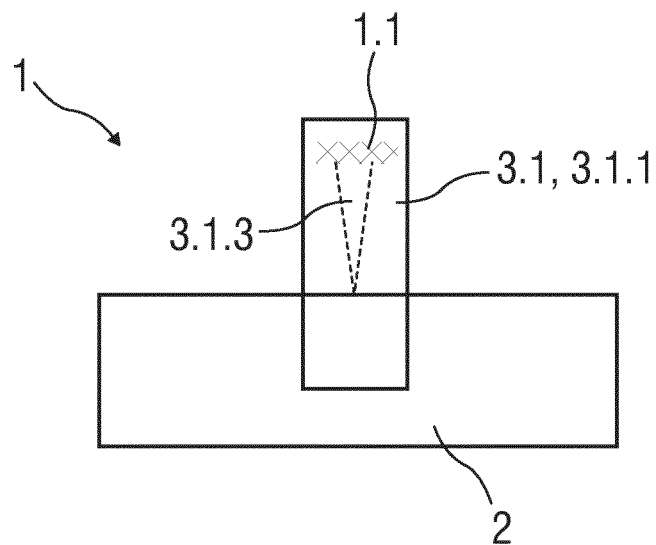
FIG. 10 is another schematic view of the sixth embodiment.

FIG. 9 is a schematic view of an exemplary sixth embodiment of a flow rate sensor 1 with an magnetic guide 3.1, e. g. a ferrite, comprising an arcuate base member 3.1.1 with a semicircular or crescent cross section and a plurality of, in particular three, inwardly directed protrusions 3.1.2, 3.1.3, 3.1.4 e. g. in the shape of spikes originating from the base member 3.1.1. FIG. 10 is another schematic view of the sixth embodiment.

Between the inward tips of the protrusions 3.1.2, 3.1.3, 3.1.4 air gaps are provided. A coil 1.1 is arranged on one of the protrusions 3.1.2, 3.1.3, 3.1.4. A tube 2 is arranged in the air gaps between the inward tips of the protrusions 3.1.2, 3.1.3, 3.1.4 such that the tube 2 is contacted by the tips of the protrusions 3.1.2, 3.1.3, 3.1.4 at angular offsets, e. g. offsets of substantially 90°. The air gaps are thus big enough ensuring that almost all magnetic flux lines M cross the tube 2 on a small area. The same set-up may be used for the first coil 1.1 with the first magnetic guide 3.1 and the second coil 1.2 with the second magnetic guide 3.2.

In an exemplary embodiment the coils 1.1, 1.2 of all illustrated embodiments may respectively consist of a number of cascaded coils, electrically connected in series.

The term "drug" or "medicament", as used herein, means a pharmaceutical formulation containing at least one pharmaceutically active compound,
wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound,
wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
wherein in a further embodiment the pharmaceutically active compound comprises at least one peptide for the treatment and/or prophylaxis of diabetes mellitus or complications associated with diabetes mellitus such as diabetic retinopathy,
wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and E have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present disclosure, which encompass such modifications and any and all equivalents thereof.

LIST OF REFERENCES 1 flow rate sensor
1.1 first coil
1.2 second coil
2 tube
2.1 first section
2.2 second section
3.1 first magnetic guide
3.1.1 base member
3.1.2 protrusion
3.1.3 protrusion
3.1.4 protrusion
3.2 second magnetic guide
4 measuring unit
D1 first diameter
D2 second diameter
M magnetic flux lines
S1 first distance
S2 second distance

The invention claimed is:

1. A flow rate sensor for determining a flow rate of a liquid within a tube, the flow rate sensor comprising:
at least one coil arranged in the vicinity of the tube in such a manner that an eddy current in the liquid due to the liquid's flowing affects an impedance of the coil;
wherein the at least one coil comprises a first coil and a second coil, the first coil arranged in the vicinity of a first section of the tube, the first section having a first diameter, the second coil arranged in the vicinity of a second section of the tube, the second section having a second diameter, and the first diameter being different from the second diameter.

2. The flow rate sensor according to claim 1, wherein the at least one coil is arranged around the tube.

3. The flow rate sensor according to claim 1, wherein the at least one coil is connected to a measuring unit adapted to determine the impedance of the at least one coil.

4. The flow rate sensor according to claim 3, wherein the measuring unit is adapted to determine a relation between a real part and an imaginary part of the impedance.

5. The flow rate sensor according to claim 1, wherein the at least one coil is arranged around a respective magnetic guide having one or two air gaps in which the tube is received.

6. The flow rate sensor according to claim 5, wherein the magnetic guide is arranged as a cup-core ferrite arranged about the tube, wherein the at least one coil is arranged within the magnetic guide.

7. The flow rate sensor according to claim 6, wherein the magnetic guide comprises an arcuate base member with a semicircular or crescent cross section and a plurality of, inwardly directed protrusions having tips, between which respective air gaps are provided, wherein at least one coil is arranged on at least one of the protrusions, wherein a tube is arranged in the air gaps between the inward tips of the protrusions such that the tube is contacted by the tips of the protrusions at angular offsets.

8. The flow rate sensor according to claim 7, wherein the protrusions are arranged as spikes originating from the base member.

9. The flow rate sensor according to claim 7, wherein the tips of the protrusions are angularly offset by substantially 90°.

10. The flow rate sensor according to claim 1, wherein the at least one coil is arranged at a predetermined distance from the tube, wherein at least in the vicinity of the coil, the tube is flexible to such an extent that the tube can expand depending on a pressure of the liquid by an amount sufficient to change the predetermined distance from the tube.

11. The flow rate sensor according to claim 10, wherein a thickness of a wall of the tube is taken into account in the predetermined distance such that the predetermined distance is between a surface of the liquid flowing through the tube and the at least one coil.

12. The flow rate sensor according to claim 1, wherein the at least one coil consists of a number of cascaded coils, electrically connected in series.

13. A drug delivery device, comprising:
a tube; and
a flow rate sensor for determining a flow rate of a liquid within the tube, the flow rate sensor comprising at least one coil arranged in the vicinity of the tube in such a manner that an eddy current in the liquid due to the liquid's flowing affects an impedance of the coil;
wherein the at least one coil comprises a first coil and a second coil, the first coil arranged in the vicinity of a first section of the tube, the first section having a first diameter, the second coil arranged in the vicinity of a second section of the tube, the second section having a second diameter, and the first diameter being different from the second diameter.

14. The device according to claim 13, wherein the at least one coil is arranged around the tube.

15. The device according to claim 13, wherein the at least one coil is connected to a measuring unit adapted to determine the impedance of the at least one coil.

16. The device according to claim 15, wherein the measuring unit is adapted to determine a relation between a real part and an imaginary part of the impedance.

17. The device according to claim 13, further comprising the liquid within the tube, wherein the liquid comprises a drug.

18. The device according to claim 17, wherein the drug comprises a pharmaceutically active compound.

* * * * *